United States Patent [19] [11] 4,297,238
Vormbrock et al. [45] Oct. 27, 1981

[54] HEMOLYSING SOLUTION PREPARING HEMOLYSED BLOOD HAVING A STABILIZED GLUCOSE CONTENT

[75] Inventors: Rolf Vormbrock; Roland Helger, both of Darmstadt, Fed. Rep. of Germany

[73] Assignee: Merck Patent Gesellschaft mit beschränkter Haftung, Darmstadt, Fed. Rep. of Germany

[21] Appl. No.: 96,347

[22] Filed: Nov. 21, 1979

[30] Foreign Application Priority Data

Nov. 22, 1978 [DE] Fed. Rep. of Germany ....... 2850603

[51] Int. Cl.³ .................. G01N 33/48; C09K 3/00
[52] U.S. Cl. .................. 252/408; 23/230 B; 23/901; 23/913; 424/3; 424/7; 435/4; 435/14
[58] Field of Search ............. 252/408; 23/230 B, 901, 23/913; 435/4, 14; 424/2, 3, 7

[56] References Cited

U.S. PATENT DOCUMENTS

| | | | |
|---|---|---|---|
| 3,519,572 | 7/1970 | Kita | 252/408 |
| 3,874,851 | 4/1975 | Wilkins et al. | 23/230 B |
| 3,918,905 | 11/1975 | Warren et al. | 23/230 B |
| 3,962,125 | 6/1976 | Armstrong | 252/408 |
| 3,964,865 | 6/1976 | Das | 252/408 |
| 3,977,995 | 8/1976 | Louderback et al. | 252/408 |
| 4,102,810 | 7/1978 | Armstrong | 252/408 |
| 4,142,857 | 3/1979 | Hcuff | 23/230 B |
| 4,185,964 | 1/1980 | Lancaster | 252/408 |
| 4,200,435 | 4/1980 | Stroupe et al. | 252/408 |

*Primary Examiner*—Teddy S. Gron
*Attorney, Agent, or Firm*—Millen & White

[57] ABSTRACT

A hemolysing solution for use in the determination of glucose in a whole blood sample which comprises (a) a buffer providing a pH of about 6-8, (b) sodium chloride, (c) a surface active agent and, (d) a chelating agent which in the presence of component (c) serves as a stabilizer against glycolysis in the hemolysate obtained by contacting the blood sample with said hemolysing solution.

7 Claims, No Drawings

HEMOLYSING SOLUTION PREPARING HEMOLYSED BLOOD HAVING A STABILIZED GLUCOSE CONTENT

BACKGROUND OF THE INVENTION

The present invention relates to a hemolysing solution and a process for the hemolysis of blood and for stabilizing the concentration of glucose in hemolysed blood.

Because of the relatively small amount of work involved, determination of the concentration of glucose in whole blood is preferred to a determination in plasma or serum. A further advantage of using whole blood is that a very small sample size (for example 20 μl) is sufficient for a determination. However, in a sample of whole blood, the enzymes contained in the erythrocytes effect glycolytic degradation of the contained glucose. For this reason, either the determination of glucose must be carried out immediately after taking the blood, or the glycolysis must be inhibited by suitable methods. Inhibition can be effected either in isotonic solution without hemolysis or after hemolysis of the sample, which can be achieved, for example, by osmotic shock or by means of digitonin.

A number of glycolysis inhibitors are known, for example, fluorides, halogenoacetates, N-alkylmaleimides, acetic acid and the like. The main disadvantage of the conventional hemolysing solutions containing these inhibitors, for use in the determination of glucose in whole blood, is that these solutions are either stable for only a limited period or do not completely inhibit the glycolysis. For example, the lifetime of the hemolysing solution of German Auslegeschrift No. 1,813,848 is only about 3–4 weeks. As a result, these solutions must be freshly prepared at short intervals of time in order to be certain that they are still completely capable of functioning.

SUMMARY OF THE INVENTION

Accordingly, it is an object of the present invention to provide a hemolysing solution for the determination of glucose in whole blood, whereby in the hemolysate glycolysis is inhibited very well and the hemolysing solution and resulting hemolysate remain stable for a virtually unlimited period of time.

Upon further study of the specification and appended claims, further objects and advantages of this invention will become apparent to those skilled in the art.

These objects have been achieved by the invention by providing a hemolysing solution comprising, in addition to a buffer and sodium chloride, a chelating agent and a surface-active agent.

In one aspect, this invention accordingly relates to a hemolysing solution for the determination of glucose in blood containing a buffer, sodium chloride, at least one chelating agent and at least one surface-active agent.

In another aspect, this invention furthermore comprises a method for the hemolysis of blood and for stabilizing the glucose concentration therein, which comprises treating whole blood with an aqueous hemolysing solution which essentially contains a buffer, sodium chloride, a chelating agent and a surface-active agent.

In still another aspect, this invention also relates to the use of a combination of at least one chelating agent and at least one surface-active agent in a hemolysing solution for use in the determination of glucose in blood.

DETAILED DISCUSSION

Surprisingly, it has been found that the combination of a chelating agent and a surface-active agent effects complete inhibition of glycolysis in a hemolysate and that a stable hemolysing solution is also obtained. Chelating agents, such as ethylenediaminetetraacetate, which are capable of inhibiting a number of glycolysis enzymes by complexing divalent metal cations, have not hitherto been used as stabilizers in hemolysing solutions because chelating agents alone cause no effective inhibition of glycolysis in blood. Rather, at an ethylenediaminetetraacetate concentration of, for example, 1 g/l, the glucose contained in the blood is degraded. In contrast, the concentration of glucose in a hemolysate prepared by the hemolysing solution of this invention is still unchanged after 12 days. An additional advantage of the hemolysing solution of this invention is that no turbidity occurs in the hemolysate.

Suitable surface-active agents for use in this invention are those capable of lysing erythrocytes and leucocytes and include ionic surface-active agents (anionic and cationic), such as sodium dodecylsulfate, cetyltrimethylammonium bromide, laurylsarcosine or tauroglycocholate, but above all non-ionic surface-active agents, preferably alkylphenol polyglycol ethers such as polyoxyethylene-10-octylphenol ether (Triton® X 100), polyoxyethylene-7.8-octylphenol ether (Triton® X 114), polyoxyethylene-10-nonylphenol ether (Renex® 690), polyoxyethylene-9-nonylphenol ether (Renex® 680).

Suitable chelating agents for use in this invention are those capable of complexing divalent metal cations such as $Mg^{2+}$, $Ca^{2+}$, $Mn^{2+}$, $Zn^{2+}$, and include, for example, ethylenediaminetetraacetate, nitrilotriacetate, cyclohexylene-1,2-dinitrilotetraacetate, diethylenetriaminepentaacetate and bis-(aminoethyl)-glycol ether-N,N,N',N'-tetraacetate, preferably ethylenediaminetetraacetate.

Combinations of such chelating agents and/or of such surface-active agents can also be employed in the hemolysing solution of this invention.

The hemolysing solution of this invention generally contains the surface-active agents in a concentration of 1–4 g/l, preferably about 2 g/l; it generally contains the chelating agents in a concentration of 0.5 to 2 g/l, preferably about 1 g/l.

Furthermore, the hemolysing solution also contains at least one buffer and sodium chloride. The buffer serves to adjust the pH value of the hemolysing solution to within the range of about 6–8, which is suitable for the determination of glucose. Appropriate buffers include the following which have proved to be suitable, for example, phosphate buffers, tris-buffers, triethanolamine buffers or imidazole buffers in a concentration of 50–500 mmoles/l. A phosphate buffer of pH value about 7.6 is preferably used, in a concentration of about 120 mmoles/l. The sodium chloride concentration should be greater than 0.8 mole/l, e.g., 0.8–3.0 mole/l and should preferably be about 1 mole/l.

To avoid microbial contamination, it is also possible to add 5–120 mmoles/l of an alkali metal azide, preferably 14 mmoles/l of sodium azide.

The hemolysis of whole blood with simultaneous stabilization of the concentration of glucose therein may be effected by a procedure in which the whole blood to be investigated is taken up in the aqueous hemolysing solution of this invention, e.g., in a volume of 25 μl of hemolysing solution per μl of whole blood sample. Thereafter, or only after some days, enzymatic determination of glucose can be carried out by fully conventional methods using this solution.

Unless otherwise specified herein, details of the hemolysis and of the glucose determination are fully conventional and are disclosed, e.g., in H. U. Bergmeyer et al., Methoden der enzymatischen Analyse, Vol. II, 3rd edition, 1974, Verlag Chemie, Weinheim, pp 1241–1246, whose disclosure is incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples all temperatures are set forth uncorrected in degrees Celsius; unless otherwise indicated, all parts and percentages are by weight.

EXAMPLE 1

Immediately after taking blood, 20 μl of the blood are taken up in 2 ml of a hemolysing solution which has the following composition:
120 mmoles/l of phosphate buffer, pH 7.6
1 mole/l of sodium chloride
14 mmoles/l of sodium azide
1 g/l of ethylenediaminetetraacetate and
2 g/l of polyoxyethylene 10-alkylphenol ether (Lutensol ® AP 10).
1 ml of this solution is pipetted into a cell and 2 ml of buffer solution of the following composition are added:
120 mmoles/l of phosphate buffer, pH 7.6
150 mmoles/l of sodium chloride
14 mmoles/l of sodium azide
2.8 mmoles/l of ethylenediaminetetraacetate
3.6 mmoles/l of nicotinamide-adenine dinucleotide and
150 U/l of mutarotase.

The extinction of the solution is measured at a wavelength of 340 nm or with an Hg 334 or Hg 365 filter. The reaction is then started by adding 20 μl of enzyme solution which contains 500 kU/l of glucose dehydrogenase. After about 5 minutes, the reaction has ended and the extinction is read. The concentration of glucose in the sample investigated is calculated from the difference in extinction ΔE according to the equation:
glucose concentration c = $\Delta E_{334} \times 889.2$ mg/dl.

The concentration of glucose remains constant for weeks, and the hemolysing solution is stable for an unlimited period.

EXAMPLE 2

The concentration of glucose in a hemolysed blood sample was determined analogously to Example 1, the hemolysate being divided into 6 parts which were each measured and evaluated at intervals of some days. For comparison, blood samples which had been treated with a hemolysing solution which contained sodium fluoride instead of the combination of chelating agent and surface-active agent were measured.

The table below shows the concentration of glucose in the various hemolysates in % of the initial value. The values were obtained with samples which contained 70 mg/dl of glucose.

| Stabilizer | Storage time (days) | | | | | |
| --- | --- | --- | --- | --- | --- | --- |
| | 1 | 2 | 5 | 7 | 9 | 12 |
| EDTA: 1.0 g/l; surface-active agent: 2.0 g/l | 102 | 103 | 103 | 102 | 102 | 103 |
| NaF, 0.5 g/l | 98.7 | 94.1 | 88.3 | 86.3 | 86.3 | 78.5 |

It can be seen from the table that the concentration of glucose in the hemolysates prepared using the homolysing solution of this invention remains constant over the period of the experiment, while the concentration of glucose in the hemolysates containing sodium fluoride decreases continuously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. In a hemolysing solution used in the determination of glucose in a whole blood sample, consisting essentially of a lysing reagent and a glycolysis inhibitor which inhibits glycolysis in the hemolysate obtained by contacting the blood sample with the hemolysing solution, the improvement wherein the hemolysing solution consists essentially of
   (a) a buffer providing a pH of about 6–8;
   (b) 0.8–3.0 moles/liter of sodium chloride;
   (c) 1–4 g/l of a surface active agent;
   (d) 0.5–2 g/l of a chelating agent which in the presence of component (c) serves as a stabilizer against glycolysis in the hemolysate; and, optionally,
   (e) an effective amount of an antimicrobial agent.

2. A hemolysing solution of claim 1, wherein the surface-active agent is a non-ionic surface-active agent.

3. A hemolysing solution of claim 2, wherein the surface-active agent is an alkylphenol polyglycol ether.

4. A hemolysing solution of claim 1, wherein the chelating agent is ethylenediaminetetraacetate, nitrilotriacetate, cyclohexylene-1,2-dinitrilotetraacetate, diethylenetriaminepentaacetate or bis-(aminoethyl)-glycol ether-N,N,N',N'-tetraacetate.

5. A hemolysing solution of claim 1 additionally comprising sodium azide as an antimicrobial agent.

6. A method for hemolysing whole blood and for stabilizing the concentration of glucose in the hemolysate, comprising treating whole blood with the aqueous hemolysing solution of claim 1.

7. The hemolysing solution of claim 1, wherein the surface active agent is an alkylphenol polyglycol ether and the chelating agent is ethylenediaminetetraacetate, nitrilotriacetate, cyclohexylene-1,2-dinitrilotetraacetate, diethylenetriaminepentaacetate or bis-(aminoethyl)-glycol ether-N,N,N',N'-tetraacetate.

* * * * *